United States Patent
Ashe, III et al.

(10) Patent No.: US 7,074,865 B2
(45) Date of Patent: Jul. 11, 2006

(54) AZABOROLYL GROUP 4 METAL COMPLEXES, CATALYSTS AND OLEFIN POLYMERIZATION PROCESS

(75) Inventors: Arthur J. Ashe, III, Ann Arbor, MI (US); Hong Yang, Ann Arbor, MI (US); Francis J. Timmers, Midland, MI (US)

(73) Assignees: Dow Global Technologies Inc., Midland, MI (US); The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 10/506,227

(22) PCT Filed: Mar. 24, 2003

(86) PCT No.: PCT/US03/09071

§ 371 (c)(1),
(2), (4) Date: Aug. 31, 2004

(87) PCT Pub. No.: WO03/087114

PCT Pub. Date: Oct. 23, 2003

(65) Prior Publication Data

US 2005/0119114 A1    Jun. 2, 2005

Related U.S. Application Data

(60) Provisional application No. 60/372,462, filed on Apr. 12, 2002.

(51) Int. Cl.
C08F 4/06 (2006.01)
C08F 4/76 (2006.01)
C08F 4/52 (2006.01)

(52) U.S. Cl. .............. 526/172; 526/161; 526/134; 526/129; 502/103; 556/7; 556/11; 556/51; 556/52

(58) Field of Classification Search .............. 556/52, 556/11; 526/172, 161, 941, 120, 134, 129
See application file for complete search history.

(56) References Cited

U.S. PATENT DOCUMENTS

| | | | |
|---|---|---|---|
| 4,530,914 A | 7/1985 | Ewen et al. | 502/113 |
| 4,871,705 A | 10/1989 | Hoel | 502/117 |
| 4,937,299 A | 6/1990 | Ewen et al. | 526/119 |
| 5,017,714 A | 5/1991 | Welborn, Jr. | 556/12 |
| 5,055,438 A | 10/1991 | Canich | 502/117 |
| 5,096,867 A | 3/1992 | Canich | 502/103 |
| 5,120,867 A | 6/1992 | Welborn, Jr. | 556/12 |
| 5,124,418 A | 6/1992 | Welborn, Jr. | 526/114 |
| 5,198,401 A | 3/1993 | Turner et al. | 502/155 |
| 5,210,352 A | 5/1993 | Alt et al. | 585/375 |
| 5,229,478 A | 7/1993 | Floyd et al. | 526/160 |
| 5,264,405 A | 11/1993 | Canich | 502/103 |
| 5,278,119 A | 1/1994 | Turner et al. | 502/155 |
| 5,278,264 A | 1/1994 | Spaleck et al. | 526/127 |
| 5,304,614 A | 4/1994 | Winter et al. | 526/127 |
| 5,324,800 A | 6/1994 | Welborn, Jr. et al. | 526/160 |
| 5,347,025 A | 9/1994 | Yamada et al. | 556/11 |
| 5,350,723 A | 9/1994 | Neithamer et al. | 502/104 |
| 5,384,299 A | 1/1995 | Turner et al. | 502/155 |
| 5,391,789 A | 2/1995 | Rohrmann | 556/11 |
| 5,391,790 A | 2/1995 | Rohrmann et al. | 556/28 |
| 5,399,636 A | 3/1995 | Alt et al. | 526/129 |
| 5,408,017 A | 4/1995 | Turner et al. | 526/134 |
| 5,455,366 A | 10/1995 | Rohrmann | 556/8 |
| 5,470,993 A | 11/1995 | Devore et al. | 556/11 |
| 5,491,207 A | 2/1996 | Hoel | 526/129 |
| 5,534,473 A | 7/1996 | Welch et al. | 502/117 |
| 5,539,124 A | 7/1996 | Etherton et al. | 548/402 |
| 5,554,775 A | 9/1996 | Krishnamurti et al. | 556/7 |
| 5,621,126 A | 4/1997 | Canich et al. | 556/9 |
| 5,684,098 A | 11/1997 | Wang et al. | 526/133 |
| 5,693,730 A | 12/1997 | Kuber et al. | 526/127 |
| 5,698,634 A | 12/1997 | Yasuda et al. | 525/269 |
| 5,703,187 A | 12/1997 | Timmers | 526/282 |
| 5,710,297 A | 1/1998 | Weller et al. | 556/11 |
| 5,712,354 A | 1/1998 | Boncella et al. | 526/127 |
| 5,714,427 A | 2/1998 | Winter et al. | 502/117 |
| 5,714,555 A | 2/1998 | Chabrand et al. | 526/127 |
| 5,728,641 A | 3/1998 | Aida et al. | 502/114 |
| 5,728,839 A | 3/1998 | Herrmann et al. | 548/103 |
| 5,753,577 A | 5/1998 | Hamura et al. | 502/113 |
| 5,756,611 A * | 5/1998 | Etherton et al. | 526/127 |
| 5,767,209 A | 6/1998 | McNally | 526/160 |
| 5,770,664 A | 6/1998 | Okumura et al. | 526/127 |
| 5,770,753 A | 6/1998 | Kuber et al. | 556/11 |
| 5,902,866 A * | 5/1999 | Nagy et al. | 526/133 |
| 5,914,408 A * | 6/1999 | Krishnamurti et al. | 548/105 |
| 6,008,394 A * | 12/1999 | Nagy et al. | 556/51 |
| 6,025,407 A * | 2/2000 | Nagy et al. | 522/29 |
| 6,121,183 A * | 9/2000 | Cribbs et al. | 502/158 |
| 6,150,297 A | 11/2000 | Campbell, Jr. et al. | 502/152 |
| 6,228,958 B1 * | 5/2001 | Nagy et al. | 526/134 |
| 6,281,155 B1 * | 8/2001 | Meyer et al. | 502/154 |
| 6,376,406 B1 | 4/2002 | Ashe, III et al. | 502/103 |
| 6,727,331 B1 * | 4/2004 | Reinking et al. | 526/161 |

FOREIGN PATENT DOCUMENTS

JP    7-258322 A   * 10/1995
WO   WO 96/34021 A1   * 10/1996

OTHER PUBLICATIONS

JP 7-258322 (abstract and translation in English).*

* cited by examiner

*Primary Examiner*—David W. Wu
*Assistant Examiner*—Rip A. Lee

(57) ABSTRACT

Metal complexes, catalysts derived therefrom, and polymerization processes using the same, characterized by the presence of one or more nitrogen and boron containing, anionic 5-membered cyclic ligand groups, especially 1,2-azaborolyl groups, are disclosed.

8 Claims, No Drawings

US 7,074,865 B2

AZABOROLYL GROUP 4 METAL COMPLEXES, CATALYSTS AND OLEFIN POLYMERIZATION PROCESS

CROSS REFERENCE STATEMENT

This application claims the benefit of U.S. Provisional Application No. 60/372,462, filed Apr. 12, 2002.

FIELD OF THE INVENTION

This invention relates to a class of metal complexes, the ligands used to prepare these metal complexes, polymerization catalysts derived therefrom, and the resulting polymerization processes using the same. More particularly, such metal complexes are characterized by the presence of one or more nitrogen and boron containing, anionic, 5-membered, cyclic ligand groups.

BACKGROUND

It is previously known in the art to use metallocene catalysts to polymerize olefins to form high molecular weight polyolefin products. Examples include Group 4 metal compounds containing one or more cyclopentdienyl ligands or derivatives thereof, as disclosed in U.S. Pat. No. 4,530,914, U.S. Pat. No. 4,871,705, U.S. Pat. No. 4,937,299, U.S. Pat. No. 5,017,714, U.S. Pat. No. 5,055,438, U.S. Pat. No. 5,096,867, U.S. Pat. No. 5,120,867, U.S. Pat. No. 5,124,418, U.S. Pat. No. 5,198,401, U.S. Pat. No. 5,210,352, U.S. Pat. No. 5,229,478, U.S. Pat. No. 5,264,405, U.S. Pat. No. 5,278,264, U.S. Pat. No. 5,278,119, U.S. Pat. No. 5,304,614, U.S. Pat. No. 5,324,800, U.S. Pat. No. 5,347,025, U.S. Pat. No. 5,350,723, U.S. Pat. No. 5,384,299, U.S. Pat. No. 5,391,790, U.S. Pat. No. 5,391,789, U.S. Pat. No. 5,399,636, U.S. Pat. No. 5,408,017, U.S. Pat. No. 5,470,993, U.S. Pat. No. 5,491,207, U.S. Pat. No. 5,455,366, U.S. Pat. No. 5,534,473, U.S. Pat. No. 5,539,124, U.S. Pat. No. 5,554,775, U.S. Pat. No. 5,621,126, U.S. Pat. No. 5,684,098, U.S. Pat. No. 5,693,730, U.S. Pat. Nos. 5,698,634, 5,703,187, 5,710,297, U.S. Pat. No. 5,712,354, U.S. Pat. No. 5,714,427, U.S. Pat. Nos. 5,714,555, 5,728,641, 5,728,839, 5,753, 577, 5,767,209, 5,770,753, 5,770,664, 5,972,020, 6,034,002, 6,040,041, 6,150,297, 6,376,406, and elsewhere.

Despite the advance in the art, particular higher use temperature, obtained by such prior art metal complexes as were disclosed in the foregoing references, there remains a desire for improved metal complexes capable of even further increase in use temperature that are still capable of forming catalyst compositions useful in producing polymers having high molecular weights and, for polymerization of ethylene/higher α-olefin copolymers, high incorporation of comonomer. The subject compositions of this invention show unexpected improvement in these desirable features.

SUMMARY OF THE INVENTION

According to the present invention there is provided a compound corresponding to the formula, $CpM(Z)_z(X)_x(L)_t(X')_{x'}$ (I), where Cp is a nitrogen and boron containing, anionic, 5-membered cyclic ligand group or substituted derivative thereof, bound to at least M;

M is a metal selected from Groups 3–10 or the Lanthanide series of the Periodic Table of the Elements;

Z is either:

a) a cyclic ligand group containing delocalized π-electrons (including a second or third anionic ligand, Cp) said Z being bonded to M by means of delocalized n-electrons and optionally also covalently bonded to Cp through a divalent bridging group, Z', or b) a divalent moiety of the formula —Z'Y—, with Z' bonded to Cp and Y covalently or coordinate covalently bonded to M, wherein, Z' is $SiR^6{}_2$, $CR^6{}_2$, $SiR^6{}_2SiR^6{}_2$, $CR^6{}_2CR^6{}_2$, $CR^6{=}CR^6$, $CR^6{}_2SiR^6{}_2$, $BR^6$, $BR^6L''$, or $GeR^6{}_2$;

Y is —O—, —S—, —NR$^5$—, —PR$^5$—; —NR$^5{}_2$, or —PR$^5{}_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —NR$^5{}_2$, and combinations thereof, said $R^6$ having up to 20 non-hydrogen atoms, and optionally, two $R^6$ groups form a ring system;

L" is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

t is a number from 0 to 2, and x' is 0 or 1.

The above compounds may exist as isolated crystals, as a mixture with other compounds, in the form of a solvated adduct, dissolved in a solvent, especially an organic liquid solvent, in the form of a dimer, or as a chelated derivative, especially wherein the chelating agent is an organic material such as ethylenediaminetetraacetic acid KEDTA).

Also, according to the present invention, there is provided a catalyst for olefin polymerization comprising:

A. i) a metal compound of formula (I), and
   ii) an activating cocatalyst,
   the molar ratio of i) to ii) being from 1:10,000 to 100:1, or
B. the reaction product formed by converting a metal compound of formula (II) to an active catalyst by use of an activating technique.

Further according to the present invention there is provided a process for the polymerization of olefins comprising contacting one or more $C_{2-20}$ olefins, including cyclic olefins, under polymerization conditions with a catalyst comprising:

A. i) a metal compound of formula (I), and
   ii) an activating cocatalyst,
   the molar ratio of i) to ii) being from 1:10,000 to 100: 1, or
B. the reaction product formed by converting a metal compound of formula (I) to an active catalyst by use of an activating technique.

The catalysts of this invention may also be supported on a solid material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

DETAILED DESCRIPTION

All reference to the Periodic Table of the Elements herein shall refer to the Periodic Table of the Elements, published and copyrighted by CRC Press, Inc., 2001. Also, any reference to a Group or Groups shall be to the Group or Groups as reflected in this Periodic Table of the Elements using the IUPAC system for numbering groups. As used herein the term "comprising" is not intended to exclude any additional component, additive or step. For purposes of United States patent practice, the contents of any patent, patent application or publication referenced herein are hereby incorporated by reference in their entirety, especially with respect to the disclosure of synthetic techniques and general knowledge in the art.

In a preferred embodiment, Cp is an 1,2-azaborolyl anionic ligand, corresponding to the formula:

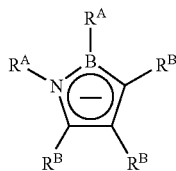

wherein, $R^A$, independently each occurrence, is a group of from 1 to 40 atoms, not counting hydrogen, selected from the group consisting of hydrocarbyl, trihydrocarbylsilyl, trihydrocarbylsilylhydrocarbyl, dihydrocarbylamino, and hydrocarbyleneamino, and optionally two $R^A$ groups may be joined together thereby forming a fused multi-ring ligand group;

$R^B$, independently each occurrence, is selected from the group consisting of hydrogen, Z' and $R^A$, where Z' is as previously defined.

Preferred metal complexes according to the present invention correspond to the formula:

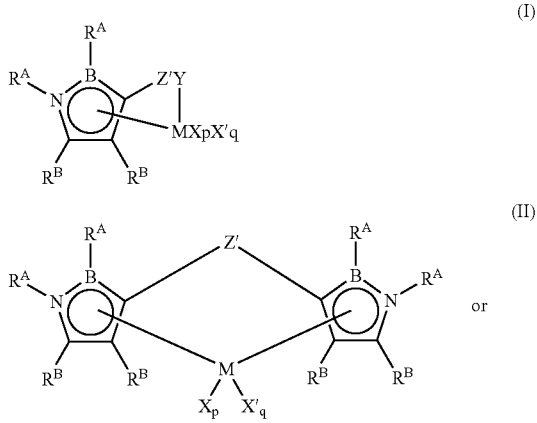

where M is a Group 4 metal that is in the +2, +3 or +4 formal oxidation state;

$R^A$ independently each occurrence is a hydrocarbyl, dihydrocarbylamino, or hydrocarbyleneamino group of from 1 to 40 atoms, not counting hydrogen, or two or more $R^A$ groups may be covalently linked together;

$R^B$ independently each occurrence is hydrogen or $R^A$;

Z' is $SiR^6{}_2$, $CR^6{}_2$, $SiR^6{}_2SiR^6{}_2$, $CR^6{}_2CR^6{}_2$, $CR^6{=}CR^6$, or $BR^6$;

Y is $-NR^5-$, $-PR^5-$; $-NR^5{}_2$, or $-PR^5{}_2$;

$R^5$, independently each occurrence, is $C_{1-20}$ hydrocarbyl;

$R^6$, independently each occurrence, is hydrogen, or $C_{1-20}$ hydrocarbyl;

X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero, 1 or 2, and is two less than the formal oxidation state of M when X is an anionic ligand, and when X is a dianionic ligand group, p is 1; and q is zero, 1 or 2.

The above complexes may exist as isolated crystals optionally in pure, enantiomeric form or as a mixture, including a racemic mixture, with other complexes, in the form of a solvated adduct, optionally in a solvent, especially an organic liquid, in the form of a dimer or as a polymeric or crosslinked polymeric product, wherein one or more $R^A$ groups are polymerized with one another or copolymerized with an ethylenically unsaturated comomomer.

Preferred compounds according to the invention are those compounds of formulas (I)–(III), wherein M is a Group 4, metal, preferably titanium for compounds of formula (I) and zirconium for compounds of formulas (II) or (III).

Preferred X groups are halo, $C_{1-10}$ hydrocarbyl or trialkylsilylalkyl groups of up to 20 caarbons, or two such X groups together form a divalent ligand group. Most preferred X groups are chloro, methyl, benzyl, trimethylsilylmethyl, or two X groups together are (dimethylsilylene)bis-(methylene).

Preferred $R^A$ groups are hydrocarbyl groups, more preferably alkyl, aryl or aralkyl groups of up to 10 carbons, or two adjacent $R^A$ groups are joined together forming a fused ring.

Preferably $R^B$ is $C_{1-10}$ hydrocarbyl;

Preferably in all embodiments of the invention, Y is $-NR^E-$ where $R^E$ is $C_{1-6}$ alkyl or cycloalkyl, preferably isopropyl, cyclohexyl, or t-butyl.

Preferred Z groups are $SiR^6{}_2$ where $R^6$ is methyl, phenyl, or $C_{1-10}$ alkylphenyl.

Preferred X' groups in all of the foregoing embodiments of the invention are carbon monoxide; phosphines, especially trimethylphosphine, triethylphosphine, triphenylphosphine and bis(1,2-dimethylphosphino)ethane; $P(OR^K)_3$, wherein $R^K$, independently each occurrence, is hydrocarbyl, silyl or silylhydrocarbyl; ethers, especially tetrahydrofuran; amines, especially pyridine, bipyridine, tetramethylethylenediamine (TEMDA), or triethylamine; olefins; and conjugated dienes having from 4 to 40 carbon atoms. Complexes including the latter X' groups, especially terminally hydrocarbyl substituted-1,3-butadienes, include those wherein the metal is in the +2 formal oxidation state.

In the foregoing compounds when p is 2, q is zero, M is in the +3 or +4 formal oxidation state, and X independently each occurrence preferably is chloride, methyl, benzyl, trimethylsilylmethyl, allyl, pyrollyl or two X groups together are 1,4-butane-diyl, 2-butene-1,4-diyl, 2,3-dimethyl-2-butene-1,4-diyl, 2-methyl-2-butene-1,4-diyl, xylyldiyl, or (dimethylsilylene)bis(methylene). Additionally, when p is 1, q is zero, M is in the +3 formal oxidation state, and X is preferably, 2-(N,N-dimethyl)aminobenzyl, 2-(N,N-dimethylaminomethyl)phenyl, allyl, or methallyl. Finally, when p is 0, q is 1, M is in the +2 formal oxidation state, and X' is 1,4-diphenyl-1,3-butadiene, 1,3-pentadiene or 2,4-hexadiene.

Highly desired metal complexes of formula (II) are ansa rac 4a,7a-azaborindenyl zirconium complexes corresponding to the formula:

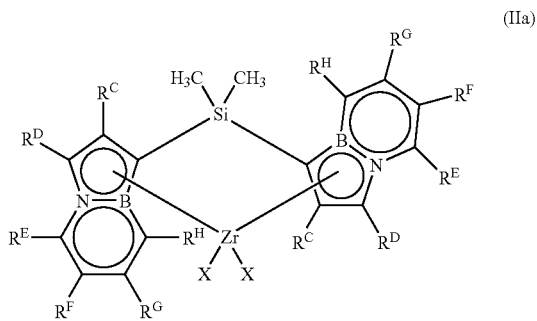

(IIa)

wherein:

$R^C$, $R^D$, $R^E$, $R^F$, $R^G$, and $R^H$ independently each occurrence are hydrogen, $C_{1-20}$ hydrocarbyl or N,N-di($C_{1-4}$ hydrocarbyl)amino; and X, independently each occurrence is chloride, methyl, benzyl, or trimethylsilylmethyl, or 2 X groups together are 1,3-pentadiene or 1,4-diphenyl-1,3-butadiene.

Preferably, $R^C$ is $C_{1-4}$ alkyl, especially methyl, $R^D$, $R^F$, $R^G$ and $R^H$ are hydrogen, and $R^E$ is phenyl or naphthyl.

The complexes can be prepared by use of well known synthetic techniques. The reactions are conducted in a suitable noninterfering solvent at a temperature from −100 to 300° C., preferably from −78 to 100° C., most preferably from 0 to 50° C. Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable.

Optionally a reducing agent can be employed to produce the lower oxidation state complexes. By the term "reducing agent" herein is meant a metal or compound which, under reducing conditions causes the metal M, to be reduced from a higher to a lower oxidation state. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal. Suitable techniques for preparing complexes of the present invention are well known to the skilled artisan and may be readily derived from techniques taught in the art.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: EP-A-277,003, U.S. Pat. No. 5,153,157, U.S. Pat. No. 5,064,802, U.S. Pat. No. 5,321,106, U.S. Pat. No. 5,721,185, U.S. Pat. No. 5,350,723, U.S. Pat. No. 5,425,872, U.S. Pat. No. 5,625,087, U.S. Pat. No. 5,883,204, U.S. Pat. No. 5,919,983, U.S. Pat. No. 5,783,512, U.S. Pat. No. 6,395,671, and WO 99/15534.

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluoro-phenylborane:alumoxane are from 1:1:1 to 1:10:30, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

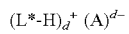
$(L^*-H)_d^+ \, (A)^{d-}$ wherein:
L* is a neutral Lewis base;
$(L^*-H)^+$ is a conjugate Bronsted acid of L*;
$A^{d-}$ is a noncoordinating, compatible anion having a charge of d−, and
d is an integer from 1 to 3.

More preferably $A^{d-}$ corresponds to the formula: $[M'Q_4]^-$;

wherein:
M' is boron or aluminum in the +3 formal oxidation state; and
Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433.

In a more preferred embodiment, d is one, that is, the counter ion has a single negative charge and is $A^-$. Activating cocatalysts comprising boron which are particularly useful in the preparation of catalysts of this invention may be represented by the following general formula:

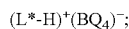
$(L^*-H)^+(BQ_4)^-$;

wherein:
L* is as previously defined;
B is boron in a formal oxidation state of 3; and
Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkylammonium salts containing one or more $C_{12-40}$ alkyl groups.

Illustrative, but not limiting, examples of boron compounds which may be used as an activating cocatalyst in the preparation of the improved catalysts of this invention are
 tri-substituted ammonium salts such as:
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6-tetrafluorophenyl)borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyltetradecylammonium tetrakis(pentafluorophenyl)borate,
dimethylhexadecylammonium tetrakis(pentafluorophenyl)borate,
dimethyloctadecylammonium tetrakis(pentafluorophenyl)borate,
methylditetradecylammonium tetrakis(pentafluorophenyl)borate,
methylditetradecylammonium(hydroxyphenyl)tris(pentafluorophenyl)borate,
methylditetradecylammonium(diethylaluminoxyphenyl)tris(pentafluorophenyl)borate,
methyldihexadecylammonium tetrakis(pentafluorophenyl)borate,
methyldihexadecylammonium(hydroxyphenyl)tris(pentafluorophenyl)borate,
methyldihexadecylammonium(diethylaluminoxyphenyl)tris(pentafluorophenyl)borate,
methyldioctadecylammonium tetrakis(pentafluorophenyl)borate,
methyldioctadecylammonium(hydroxyphenyl)tris(pentafluorophenyl)borate,
methyldioctadecylammonium(diethylaluminoxyphenyl)tris(pentafluorophenyl)borate,
mixtures of the foregoing,
dialkyl ammonium salts such as:
di-(i-propyl)ammonium tetrakis(pentafluorophenyl)borate, methyloctadecylammonium tetrakis(pentafluorophenyl)borate, methyloctadodecylammonium tetrakis(pentafluorophenyl)borate, and dioctadecylammonium tetrakis(pentafluorophenyl)borate;
tri-substituted phosphonium salts such as:
triphenylphosphonium tetrakis(pentafluorophenyl)borate,
methyldioctadecylphosphonium tetrakis(pentafluorophenyl)borate, and tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and di(octadecyl)oxonium tetrakis(pentafluorophenyl)borate;
di-substituted sulfonium salts such as:

di(o-tolyl)sulfonium tetrakis(pentafluorophenyl)borate, and methylcotadecylsulfonium tetrakis(pentafluorophenyl) borate.

Preferred (L*-H)⁺ cations are methyldioctadecylammonium and dimethyloctadecylammonium. The use of the above Bronsted acid salts as activating cocatalysts for addition polymerization catalysts is known in the art, having been disclosed in U.S. Pat. No. 5,064,802, U.S. Pat. No. 5,919,983, U.S. Pat. No. 5,783,512 and elsewhere.

Another suitable ion forming, activating cocatalyst comprises a salt of a cationic oxidizing agent and a noncoordinating, compatible anion represented by the formula:

$$(Ox^{e+})_d(A^{d-})_e.$$

wherein:

$Ox^{e+}$ is a cationic oxidizing agent having a charge of e+;

e is an integer from 1 to 3; and $A^{d-}$ and d are as previously defined.

Examples of cationic oxidizing agents include: ferrocenium, hydrocarbyl-substituted ferrocenium, $Ag^{+}$, or $Pb^{+2}$. Preferred embodiments of $A^{d-}$ are those anions previously defined with respect to the Bronsted acid containing activating cocatalysts, especially tetrakis(pentafluorophenyl) borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

$$ⓒ^+ A^-$$

wherein:

ⓒ⁺ is a $C_{1-20}$ carbenium ion; and $A^-$ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

$$R_3Si(X')_q^+A^-$$

wherein:

R is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula:

$$(A^{1+a^1})_{b^1}(Z^1J^1_{j^1})^{-c^1}_{d^1},$$

wherein:

$A^1$ is a cation of charge $+a^1$, $Z^1$ is an anion group of from 1 to 50, preferably 1 to 30 atoms, not counting hydrogen atoms, further containing two or more Lewis base sites;

$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

$$A^{1+}\left[J^1-N\overset{R^8}{\underset{R^8\ \ \ R^8}{\bigcirc}}N-J^1\right], \quad A^{1+}\left[J^1-N\overset{R^8}{\underset{(R^8)_2\ (R^8)_2}{\bigcirc}}N-J^1\right] \text{ or}$$

$$A^{1+}\left[J^1-N\overset{R^8}{\underset{R^8\ \ \ R^8}{\bigcirc}}N-J^1\right],$$

wherein:

$A^{1+}$ is a monovalent cation as previously defined, and preferably is a trihydrocarbyl ammonium cation, containing one or two $C_{10-40}$ alkyl groups, especially the methylbis (tetradecyl)ammonium- or methylbis(octadecyl)ammonium- cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium- salts of: bis (tris(pentafluorophenyl)borane)imidazolide, bis(tris (pentafluorophenyl)borane)-2-undecylimidazolide, bis(tris (pentafluorophenyl)borane)-2-heptadecylimidazolide, bis (tris(pentafluorophenyl)borane)-4,5-bis(undecyl) imidazolide, bis(tris(pentafluorophenyl)borane)-4,5-bis (heptadecyl)imidazolide, bis(tris(pentafluorophenyl)borane) imidazolinide, bis(tris(pentafluorophenyl)borane)-2-undecylimidazolinide, bis(tris(pentafluorophenyl)borane)-2-heptadecylimidazolinide, bis(tris(pentafluorophenyl) borane)-4,5-bis(undecyl)imidazolinide, bis(tris (pentafluorophenyl)borane)-4,5-bis(heptadecyl) imidazolinide, bis(tris(pentafluorophenyl)borane)-5,6-dimethylbenzimidazolide, bis(tris(pentafluorophenyl) borane)-5,6-bis(undecyl)benzimidazolide, bis(tris (pentafluorophenyl)alumane)imidazolide, bis(tris (pentafluorophenyl)alumane)-2-undecylimidazolide, bis(tris (pentafluorophenyl)alumane)-2-heptadecylimidazolide, bis (tris(pentafluorophenyl)alumane)-4,5-bis(undecyl) imidazolide, bis(tris(pentafluorophenyl)alumane)-4,5-bis (heptadecyl)imidazolide, bis(tris(pentafluorophenyl) alumane)imidazolinide, bis(tris(pentafluorophenyl) alumane)-2-undecylimidazolinide, bis(tris (pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis (heptadecyl)imidazolinide, bis(tris(pentafluorophenyl)alumane)-5,6-dimethylbenzimidazolide, and bis(tris (pentafluorophenyl)alumane)-5,6-bis(undecyl) benzimidazolide.

A further class of suitable activating cocatalysts include cationic Group 13 salts corresponding to the formula:

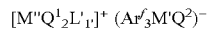

$$[M''Q^1_2L'_{1'}]^+ \ (Ar^f_3M'Q^2)^-$$

wherein:

M'' is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

1' is a number greater than zero indicating the number of Lewis base moieties, L', and $Ar^f$ independently each occurrence is an anionic ligand group; preferably $Ar^f$ is selected from the group consisting of halide, $C_{1-20}$ halohydrocarbyl, and $Q^1$ ligand groups, more preferably $Ar^f$ is a fluorinated hydrocarbyl moiety of from 1 to 30 carbon atoms, most preferably $Ar^f$ is a fluorinated aromatic hydrocarbyl moiety of from 6 to 30 carbon atoms, and most highly preferably $Ar^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula: $[M''Q^1_2L'_{1'}]^+ (Ar^f_3BQ^2)^-$, wherein M'' is aluminum or gallium; $Q^1$ is $C_{1-20}$ hydrocarbyl, preferably $C_{1-8}$ alkyl; $Ar^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is employed in large quantity, generally at least 100 times the quantity of metal complex on a molar basis. Tris(pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, and norbornadiene. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a non-conjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}$:1 to $10^{-1}$:1, more preferably from $10^{-9}$:1 to $10^{-5}$:1.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The present catalyst compositions may be advantageously employed to prepare olefin polymers having improved processing properties by polymerizing ethylene alone or ethylene/α-olefin mixtures with low levels of a "H" branch inducing diene, such as norbornadiene, 1,7-octadiene, or 1,9-decadiene. The unique combination of elevated reactor temperatures, high molecular weight (or low melt indices) at high reactor temperatures and high comonomer reactivity advantageously allows for the economical production of polymers having excellent physical properties and processability. Preferably such polymers comprise ethylene, a $C_{3-20}$ α-olefin and a "H"-branching comonomer. Preferably, such polymers are produced in a solution process, most preferably a continuous solution process.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluoro-phenyl)borate, such as an ammonium salt of (4-hydroxy-3,5-ditertiarybutylphenyl) tris-(pentafluorophenyl)borate or (4-hydroxyphenyl)-tris (pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than 0.5, preferably less than 0.2, more preferably less than 0.05, even more preferably less than 0.02 and may even be less than 0.01.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc. HRMS refers to high resolution mass spectroscopy.

All solvents were purified using the technique disclosed by Pangborn et al, *Organometallics*, 15, 1518–1520, (1996). All compounds, solutions, and reactions were handled under an inert atmosphere (dry box). $^1$H and $^{13}$C NMR shifts were referenced to internal solvent resonances and are reported relative to TMS.

Example 1

Preparation of (η-1-Ethyl-2-phenyl-1H-1,2-azaborolyl)(η-pentamethyl-cyclopentadienyl)zirconium(IV) dichloride

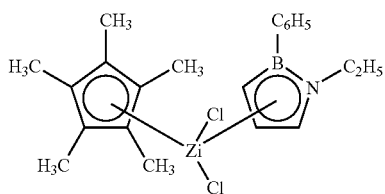

A) (N-Allyl-N-ethylamino)vinylphenylborane

The title product was obtained by reaction of N-allyl-N-ethylamine with vinylphenylboron in the presence of triethylamine substantially according to the procedure of *Org. Lett.* 2, p2089 (2000). The product was obtained by vacuum distillation as a clear colorless liquid (84 percent), bp 67–70° C. at 0.05 torr.

B) 1,5-Dihydro-1-ethyl-2-phenyl-1,2-azaborole

A solution of (N-Allyl-N-ethylamino)vinylphenylborane (17.2 g, 86.4 mmol) in 120 mL of $CH_2Cl_2$ was added to a solution of bis(tricyclohexylphosphine)benzylidene ruthenium (IV) dichloride (Grubbs' catalyst) (3.55 g, 4.31 mmol) in 40 mL of $CH_2Cl_2$ at 25° C. The mixture was stirred at 25° C. for 10 hours after which the color had changed from purple-red to dark brown. The solvent was removed in vacuo and the product (12.6 g, 85 percent) as a clear colorless liquid, bp 60° C. at 0.05 torr.

$^1$H NMR ($C_6D_6$, 400 MHz): δ 7.75 (d, 2H, J=8.0 Hz, ArH), 7.33 (t, 2H, J=8.0 Hz, ArH), 7.25 (t, 1H, J=8.0 Hz, ArH), 6.93 (d, 1H, J=8.1 Hz, vinyl), 6.60 (d, 1H, J=8.1 Hz, vinyl), 3.51 (m, 2H, $NCH_2CH$=), 3.26 (q, 2H, J=7.0 Hz, Et), 0.94 (t, 3H, J=7.0 Hz, Et).

$^{13}$CNMR ($C_6D_6$, 100.6 MHz): δ 148.5, 134.1, 132.3, 132.1, 128.9, 128.1, 127.6, 60.3 ($NCH_2C$=), 41.4 (Et), 16.7 (Et).

$^{11}$B N ($C_6D_6$, 115.5 MHz): δ 39.4.

HRMS (EI, m/z): calculated for $C_{12}H_{14}{}^{11}BN$ (M$^+$), 171.1219; found, 171.1224.

Analysis: Calculated for $C_{11}H_{14}BN$: C, 77.24; H, 8.25; N, 8.19. Found: C, 77.83; H, 8.45; N, 7.68.

C) Lithium 1-ethyl-2-phenyl-1,2-azaborolide 1,5-Dihydro-1-ethyl-2-phenyl-1,2-azaborole (5.0 g, 29.2 mmol) was dissolved in 15 mL of ether at −78° C. To this was added a solution of lithiumdiisopropylamide (3.13 g, 29.2 mmol) in 15 mL of ether. The mixture was stirred at −78° C. for 2 hours and at 25° C. for 10 hours. After removal of the solvent the residue was washed with 3×20 mL of pentane. The residue was dried under vacuum to give the product as a light yellow powder (3.9 g, 77 percent).

$^1$H NMR (THF-d8, 400 MHZ): δ 7.51 (d, 2H, J=8.0 Hz, ArH), 7.05 (t, 2H, J=8.0 Hz, ArH), 6.87 (t, 1H, J=8.0 Hz, ArH), 5.91 (m, 1H, H4), 5.86 (m, 1H, $H_5$), 4.16 (m, 1H, $H_3$), 3.78 (q, 2H, J=7.0 Hz, Et), 1.27 (t, 3H, J=7.0 Hz, Et).

$^{13}$C NMR (THF-d8, 100.6 MHz): δ 133.9, 127.2, 123.8, 112.8, 111.9, 86.5 (br), 43.2 (Et), 19.6 (Et).

$^{11}$B NMR (THF-d8, 115.5MHz): δ 29.4.

D) (η-1-ethyl-2-phenyl-1H-1,2-azaborolyl)(η-pentamethyl-cyclopentadienyl)zirconium(IV)dichloride A solution of lithium 1-ethyl-2-phenyl-1,2-azaborolide (0.42 g, 2.37 mmol) in 10 mL of ether was added to a suspension of pentamethylcyclopentadienylzirconium trichloride (0.78 g, 2.34 mmol) in 10 mL of ether at −78° C. Stirring was maintained for 12 h as the mixture was slowly warmed to 25° C. The solvent was removed in vacuo and residue was washed with pentane and dried, affording the product (0.54 g, 56 percent) as a yellow powder.

$^1$H NMR (400 MHz, $C_6D_6$): δ 7.79 (dd, J=8.2, 1.4 Hz, 2H, ArH); 7.29 (t, J=7.3 Hz, 2H, ArH); 7.19 (t, J=7.4 Hz, 1H, ArH); 6.24 (t, J=2.6 Hz, 1H, ring CH); 5.33 (dd, J=4.5, 2.7 Hz, 1H, ring CH); 4.62 (dd, J=4.9, 2.7 Hz, H, ring CH); 4.06 (dq, J=14.0, 7.0 Hz, 1H, NCH); 3.86 (dq, J=14.0, 7.0 Hz, 1H, NCH'); 1.77 (s, 15H, CpMe) 0.89 (t, J=7.3 Hz, 3H, $NCH_2CH_3$).

$^{13}$C NMR (100.6 MHz, $C_6D6$): δ 134.5, 128.5, 127.7, 127.5, 123.5, 114.1, 44.1, 16.8, 12.2. $^{11}$B NMR (115.6 MHz, $C_6D6$): δ 33.7.

HRMS: Calculated for $C_{21}H_{28}{}^{11}B$ $^{35}Cl_2NZr$, 465.0740. Found: 465.0740.

Analysis: Calculated for $C_{21}H_{28}BCl_2NZr$: C, 53.96; H, 6.05; N, 3.00. Found: C, 52.52; H, 6.41; N, 2.79.

Example 2

Preparation of bis(1-ethyl-2-phenyl-1,2-azaborolyl)zirconium dichloride

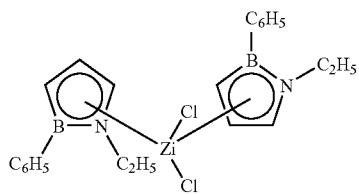

A suspension of lithium (1-ethyl-2-phenyl-1,2-azaborolide) (1C), 0.80 g, 4.52 mmol) in 25 mL of ether was added to a suspension of $ZrCl_4$ (0.51 g, 2.19 mmol) in 25 mL of ether at −50° C. The mixture was stirred for 8 h, during which time the mixture warmed to 25° C. The mixture was filtered through diatomaceous earth and the solvent was removed in vacuo. The residue was washed with ether and dried to obtain the desired product (0.65 g, 59 percent). The $^1$H NMR spectra indicated that the product is a mixture of two diasteromers in the ratio of 4:1. Spectral signals for the major isomer are reported.

$^1$H NMR (400 MHz, C$_6$D$_6$): δ 7.76 (d, J=8.1 Hz, 4H, ArH), 7.21 (m, 6H, ArH); 6.25 (m, 2H, ring CH); 6.07 (m, 2H, ring CH), 4.80 (m, 2H, ring CH), 3.75 (dq, J=14.2, 7.1 Hz, 2H, NCH); 3.57 (dq, J=14.2, 7.1 Hz, 2H, NCH), 0.75 (t, J=7.31 Hz, 6H).

$^{13}$C NMR (100.5 MHz, CDCl$_3$): δ 134.4; 128.9, 128.1, 123.3, 120.1, 98 (br), 45.5, 17.6.

$^{11}$B NMR (115.6 MHz, C$_6$D$_6$): δ 3.7.

HRMS: Calculated for C$_{22}$H$_{26}$$^{11}$B$_2$ $^{35}$Cl$_2$N$_2$Zr: 500.0606. Found: 500.0604.

Analysis: Calculated for C$_{22}$H$_{26}$B$_2$Cl$_2$N$_2$Zr: C, 52.61; H, 5.23; N, 5.58. Found: C, 51.36; H, 5.18; N, 5.32.

Example 3

Preparation of [(η$^5$-cyclopentadien-1-yl)(η$^5$-1-ethyl-2-phenyl-1H-1,2-azaborol-3-yl)dimethylsilane]zirconium dichloride

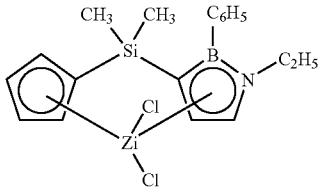

A) 1-Ethyl-3-chlorodimethylsilyl-2,3-dihydro-2-phenyl-1H-1,2-azaborole

A solution of Me$_2$SiCl$_2$ (0.69 mL, 0.73 g, 5.65 mmol) in 15 mL of ether was added dropwise to a solution of lithium (1-ethyl-2-phenyl-1,2-azaborolide) (Ex. 1C), 1.0 g, 5.65 mmol) in 25 mL of ether at –78° C. When the addition was complete, the mixture was warmed slowly to 25° C. and stirred for 10 h. The solvent was removed under reduced pressure and the residue was extracted with pentane. The extracts were filtered through diatomaceous earth and the solvent was removed in vacuo leaving the product as an orange oil (1.38 g, 92 percent).

$^1$H NMR (400 MHz, CDCl$_3$): δ 7.40 (dd, J=7.7, 1.8 Hz, 2H, ArH), 7.23 (m, 3H, ArH); 6.34 (dd, J=3.8, 1.3 Hz, 1H, ViH); 5.70 (dd, J=3.8, 2.4 Hz, 1H, ViH); 3.30 (m, 1H, NCH); 3.12 (m, 1H, NCH'); 2.64 (br s, 1H, BCH); 0.94 (t, J=7.1 Hz, 3H, CMe), 0.14 (s, 3H, SiMe'), 0.09 (s, 3H, SiMe').

$^{13}$C NMR (100.6 MHz, C$_6$D$_6$): δ 139.1, 133.5 (Ph), 128.8 (Ph), 127.9 (Ph), 112.2, 41.1. (NCH$_2$), 39 (br, BCH), 17.3 (CMe), 2.4 (SiMe), 0.2 (SiMe').

$^{11}$B NMR (115.5 MHz, C$_6$D$_6$): δ 44.6.

HRMS. Calculated for C$_{13}$H$_{19}$ $^{11}$B $^{35}$ClNSi: 263.1068. Found: 263.1078.

Analysis: calculated for C$_{13}$H$_{19}$BClNSi: C, 59.21; H, 7.28; N, 5.31. Found: C, 59.04; H, 7.12; N, 5.46.

B) 1-Ethyl-3-[cyclopentadienyldimethylsilyl]-2,3-dihydro-2-phenyl-1H-1,2-azaborole A solution of cyclopentadienyl lithium (0.16 g, 2.27 mmol) in 10 mL of THF was added slowly to a solution of 1-ethyl-3-chlorodimethylsilyl-2,3-dihydro-2-phenyl-1H-1, 2-azaborole (0.60 g, 2.27 mmol) in 10 mL of THF at –50° C. The reaction mixture wag slowly warmed to 25° C. and stirred for 12 h. The solvent was removed in vacuo and the residue was extracted with pentane. Solvent was removed from the extracts leaving the desired product as a brown oil (0.58 g, 87 percent).

H NMR (400 MHz, C$_6$D$_6$): δ 7.40 (dd, J=7.9, 1.2 Rz, 2H, ArH); 7.16 (t, J=7.0 Hz, 2H, ArH); 7.10 (t, J=7.0 Hz, IR, ArH); 6.54 (br s, 2H, Cp); 6.50 (br s, 2H, Cp), 6.28 (dd, J=4.0, 1.1 Hz, 1H, ViH); 5.54 (dd, J=3.9, 2.8 Hz, 1H, ViH); 3.30 (m, 1H, NCH); 3.22 (br s, 1H, Cp); 3.10 (m, 1H, N CH'), 2.45 (dd, J=2.6, 1.1 Hz, 1H, BCH); 0.92 (t, J=7.1 Hz, 3H, CMe); –0.13 (s, 3H, SiMe); –0.35 (s, 3H, SiMe').

$^{13}$C NMR (C$_6$D$_6$, 100.6 mHz): δ 137.8, 133.5, 133.0, 130.4, 128.6, 128.0, 127.7, 113.4, 67.5, 41.1, 37.4 (bn), 25.6, 17.5, –4.8, –4.9.

$^{11}$B NMR (115.5 Hz, C$_6$D$_6$): δ 45.0.

HRMS: Calculated for C$_{18}$H$_{24}$ $^{11}$BNSi: 293.1771. Found: 293.1774.

C) [(η$^5$-cyclopentadien-1-yl)(η$^5$-1-ethyl-2-phenyl-1H-1,2-azaborol-3-yl)dimethylsilane]zirconium dichloride A solution of lithiumdiisopropylamide (0.66 g, 6.20 mmol) in THF (20 mL) was added to a solution of 1-ethyl-3-[cyclopentadienyldimethylsilyl]-2,3-dihydro-2-phenyl-1H-1,2-azaborole (0.91 g, 3.10 mmol) in 20 mL of THF at –78° C. The mixture was slowly warmed to 25° C. and allowed to stir for 12 h. After removal of the solvent in vacuo the residue was washed with pentane. The solid was dissolved in 20 mL of toluene and added to a suspension of ZrCl$_4$ (0.69 g, 3.00 mmol) in 10 mL of toluene at –50° C. When the addition was complete, the mixture was allowed to warm to 25° C. with stirring for 12 h. The solvent was removed under reduced pressure and the product was extracted with ether, which was then filtered through diatomaceous earth. Removal of solvent left a yellow solid, which was washed with pentane. The yield was 0.80 g (59 percent).

$^1$H NMR (300 Mz, CDCl$_3$): δ 7.57 (m, 2H, ArH); 7.38 (d, J=2.5 Hz, 1H, C$_3$H$_2$BN), 7.26 (m, 3H, ArH), 6.98 (m, 1H, Cp); 6.87 (m, 1H, Cp); 6.00 (m, 1H, Cp); 5.92 (d, J=2.5 Hz, 1H, C$_3$H$_2$BN); 5.88 (m, 1H, Cp); 4.08 (dq, J=13.7,7.1 Hz, 1H, NCH); 3.75 (dq, J=13.7, 7.1 Hz, NCH); 1.21 (t, J=7.3 Hz, 3H, CH$_3$C); 0.62 (s, 3H, SiMe); 0.37 (s, 3H, SiMe').

$^{13}$C NMR (100.6 MHz, CDCl$_3$): δ 140.4; 135.6; 129.5; 128.6; 127.3; 120.9; 120.6; 112.5; 110.4; 44.1; 16.8; –2.3; –3.5.

$^{11}$B NMR (115.6 MHz, CDCl$_3$): δ 34.6.

HRMS: Calculated for C$_{18}$H$_{22}$$^{11}$BCl$_2$NSiZr: 451.0039. Found: 451.0016.

Analysis: Calculated for C18H$_{22}$BCl$_2$NSiZr: C, 47.68; H, 4.90; N, 3.09. Found: C, 47.92; H, 5.17; N, 3.11.

Example 4

Preparation of Rac-[bis(η$^5$-1-ethyl-2-phenyl-1H-1, 2-azaborol-3-yl)-dimethylsilane]zirconium dichloride

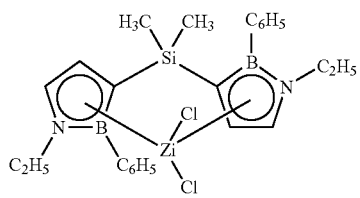

A) Bis[1-ethyl-2,3-dihydro-2-phenyl-1H-1,2-azaborol-3-yl] dimethylsilane

The title compound was prepared in the same manner as Example 3B) from lithium (1-ethyl-2-phenyl-1,2-azaborolide) (1C), 0.41 g, 2.31 mmol) in 15 mL of THF and 1-ethyl-3-chlorodimethylsilyl-2,3-dihydro-2-phenyl-1H-1, 2-azaborole (Ex. 3A), 0.01 g, 2.31 mmol) in 15 mL of THF. The product was obtained as a yellow oil (0.85 g, 92 percent).

$^1$H NMR (400 MHz, $C_6D_6$): δ 7.40 (dd, J=8.0, 1.5 Hz, 4H, ArH); 7.18 (t, J=7.3 Hz, 4H, ArH); 7.12 (t, J=7.3 Hz, 2H, ArH); 6.29 (dd, J=4.0, 1.1 Hz, 2H, ViH); 5.58 (dd, J=3.6, 1.1 Hz, 2H, ViH); 3.26 (m, 2H, NCR); 3.11 (m, 2H, NCH); 2.43 (dd, J=2.6, 1.1 Hz, 2H, BCH); 0.89 (t, J=7.0 Hz, 6H, CMe); −0.18 (s, 3H, SiMe); −0.42 (s, 3H, SiMe).

$^{13}$C NMR (100.6 MHz, $CDCl_3$): δ 137.4, 133.5 (Ph); 128.3 (Ph); 127.7 (Ph), 113.7, 41.2 ($NCH_2$),37.2 (br, BCH), 17.9 (CMe), −4.3 (SiMe), −4.4 (SiMe).

$^{11}$B ($CDCl_3$, 115.5 Mz): δ 4.52.

HRMS: Calculated for $C_{29}H_{32}$ $^{11}B_2N_2Si$: 398.2520. Found: 398.2516.

B) Rac-[bis($\eta^5$-1-ethyl-2-phenyl-1H-1,2-azaborol-3-yl) dimethylsilane]zirconium dichloride A solution of lithium diisopropylamide (0.46 g, 4.26 mmol) in 10 mL of THF was added to a solution of bis[1-ethyl-2,3-dihydro-2-phenyl-1H-1,2-azaborol-3-yll-dimethylsilane (0.85 g, 2.13 mmol) in 10 mL of THF at −78° C. The mixture was slowly warmed to 25° C. and stirred for 8 h. The solvent was removed in vacuo and the residue was washed with 3×10 mL of pentane. This solid was dissolved in 10 mL of toluene and the resulting solution was added to a suspension of $ZrCl_4$ (0.49 g, 2.13 mmol) in 10 mL of toluene at −50° C. Stirring was continued for 12 h and the mixture was warmed slowly to 25° C. The solvent was removed in vacuo and the product was dissolved in ether which was filtered through diatomaceous earth. Removal of the solvent under reduced pressure gave the product as a orange solid. The yield was 0.80 g (68 percent).

$^1$H NMR (300 Mz, $C_6D_6$): δ 7.70 (dd, J=8.1, 1.5 Hz, 4H, ArH); 7.25 (t, J=7.6 Hz, 4H, ArH); 7.15 (t, J=7.4 Hz, 2H, ArH); 6.83 (d, J=2.5 Hz, 2H, $C_3H_2BN$); 5.86 (d, J=2.5 Hz, 2H, $C_3H_2BN$); 3.75 (dq, J=13.4, 6.9 Hz, 2H, NCH); 3.38 (dq, J=13.4, 6.9 Hz, 2H, NCH'); 0.64 (t, J=7.2 Hz, 6H, $CH_3$), 0.32 (s, 6H, SiMe).

$^{13}$C NMR (100.6 MHz, $CDCl_3$): δ 135.6, 131.4, 128.5, 127.6, 119.7, 44.7, 17.2, −1.0.

$^{11}$B (115.6 MHz, $CDCl_3$): δ 31.8.

HRMS: Calculated for $C_{24}H_{30}{}^{11}B_2$ $^{35}Cl_2N_2SiZr$: 556.0788. Found: 556.0770.

Analysis: calculated for $C_{24}H_{30}B_2Cl_2N_2SiZr$: C, 51.62; H, 5.43; N, 5.02. Found: C, 51.32; H, 5.39; N, 5.08.

Example 5

Preparation of (4,7-Dihydro-3e,7a-azaborindenyl) (pentamethyl-cyclopentadienyl)zirconium dichloride

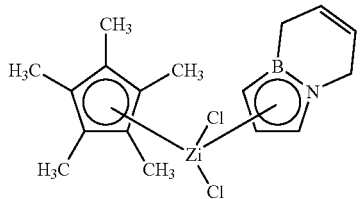

A) Allyl(N,N-diallylamino)boron chloride

A solution of allyltributyltin (62.2 g, 0.19 mol) in 50 mL of hexane was added dropwise to a solution of $BCl_3$ (24.8 g, 0.21 mol) in 120 mL of hexane at −78° C. After the reaction mixture was stirred at −78° C. for 1 hour, it was allowed to warm to 25° C. for 2 hours followed by recooling to −78° C. Then diallylamine (23.5 mL, 0.19 mol) was added dropwise followed by triethylamine (26.7 mL, 0.19 mol). The mixture was stirred for 12 hours while it slowly warmed to 25° C. The solvent was removed under reduced pressure and the product (33.1 g, 95 percent) was obtained by distillation (bp=38° C. at 0.1 torr).

HRMS: Calculated for $C_9H_{15}{}^{11}B^{35}ClN$: 183.0986. Found: 183.0984.

$^1$H NMR ($C_6D_6$, 300 MHz): δ 1.90(d, J=7.1 Hz, $2CH_2B$), 3.32(d, J=5.2 Hz, 2H, $CH_2N$), 3.65(d. J=5.5Hz, 2H, $CH_2N^1$), 4.8–5.0(m, 6H, 3ViH), 5.3(m, 1H, ViH), 5.5 (m, 1H, ViH), 5.9(m, 1H, ViH).

$^{11}$B NMR ($C_6D_6$, 115.5 MHz): δ 38.1

$^{13}$C NMR ($C_6D_6$, 75.5 MHz): δ 50.5, 51.3, 115.0, 116.0, 116.2, 134.9, 135.0

B) Allyl(N,N-diallylamino)vinyl borine

A solution of vinylmagnesium bromide, which had been prepared from vinylbromide (23.5 g, 0.22 mol) and magnesium (5.3 g, 0.2 mol) in 250 mL of THF, was added to a solution of allyl(N,N-diallylamino)boron chloride (33.1 g, 0.18 mol) in 100 mL of THF at −78° C. The reaction mixture was stirred for 10 hours and allowed to warm slowly to 25° C. The solvent was removed under reduced pressure and the residue was extracted with pentane. The solvent was removed from the extracts and the product (26.5 g, 84 percent) was distilled (bp=36° C. at 0.1 torr).

HRMS: Calculated for $C_{11}H_{18}{}^{11}BN$: 175.1532. Found 175.1529.

$^1$H NMR ($C_6D_6$, 400 MHz): δ 1.94(d, J=7.3 Hz, 2H, $BCH_2$), 3.48 (broad s, 4H, $2NCH_2$), 4.88 (m, 6H, $ViCH_2$), 5.46 (m, 2H, ViH), 5.8–6.0 (m, 3H, ViH), 6.26 (dd, J=19.6, 13.7 Hz, 1H BCH).

$^{11}$B NMR ($C_6D_6$, 115 MHz): δ 39.7

$^{13}$C NMR ($CH_2D_2$, 125.7 MHz): δ 24 (broad), 51, 51.4, 113.3, 115.2, 115.5, 131.4, 135.1, 136.5, 137.6, 139(broad)

C) 4.7-Dihydro-4a,7a-azaborindene

A solution of allyl(N, N-diallylamino)vinyl borine (26.5, 0.15 mol) in 50 mL of $CH_2Cl_2$ was added to a solution of $(Cy_3P)_2$ $(PhCH)RuCl_2$ (6.23 g, 75 Mmol) in 150 mL of $CH_2Cl_2$ and the resulting mixture was heated to reflux for 24 hours. The solvent was removed under reduced pressure and the residue was distilled to obtain the product (13.9 g, 78 percent) bp =27° C. at 0.1 torr.

HRMS Calculated for $C_7H_{10}{}^{11}BN$: 119.0906. Found 119.0906.

$^1$H NMR ($C_6D_6$, 400 MHz): δ 1.68 (broad, s, 2H, $CH_2B$), 3.19(d, J=3Hz, 2H, $CH_2N$), 3.46 (m, 2H, $CH_2N^1$), 5.50 (d, m, J=10.3 Hz, 1H, ViH), 5.84 (d, m, J=10.3 Hz, 1H, ViH), 6.22 (d, J=7.7 Hz, 1H, ViH), 6.78 (d, J=8.1 Hz, 1H, ViH).

$^{11}$B NMR ($C_6D_6$, 115.5 MHz): δ 37.7.

$^{13}$C NMR ($C_6D_6$, 100.5 MHz): δ 13.0 (broad), 45.6, 60.0, 124.8, 125.8, 133 (broad), 148.

D) (4,7-Dihydro-3a,7a-azaborindenyl)(pentamethylcyclopentadienyl)zirconium dichloride A 0.5M solution of $KN(SiMe_3)_2$ (6.80 mL, 3.40 mmol) in toluene was added dropwise to a solution of 4,7-dihydro-4a,7a-azaborindene in 10 mL toluene at −78° C. The mixture was stirred 10 hours and allowed to slowly warm to 25° C. The solution was filtered and the solid was washed successively with 3×5 mL of toluene and 3×10 mL of pentane.

Ethyl ether (15 mL) was added to the solid and the resulting suspension was added to a solution of pentamethylcyclopentadienyl zirconium trichloride (1.12 g, 3.36 mmol) in 10 mL of ether at −50° C. The resulting orange suspension was stirred 10 hours and allowed to warm slowly to 25° C. After removal of the volatiles in vacuum the product was extracted with ether. The extracts were slowly concentrated by partial removal of solvent and the resulting solution was stored at −20° C. until yellow crystals (0.71 g, 51 percent) were obtained. The structure was confirmed by X-ray crystallography.

$^1$H NMR (CDCl$_3$, 400 MHz): δ 1.70(dm, J=20 Hz, 1H, C(7)H), 2.00(dm, J=20 Hz, 1H, C(7)H$^1$), 2.00(s, 15H, CpMe), 4.04(dm, J=17.9Hz, 1H, C(4)H), 4.14(dd, J=4.9, 2.4 Hz, 1H, C(1)H), 4.62(dm, J=17.9 Hz, 1H, C(4)H$^1$), 5.54 (dm, J=10.6 Hz, 1H, ViH, 5.82(dd, J=5.1, 2.5 Hz, 1H, C(2)H), 5.89(dm, J=10.6 Hz, 1H, ViH), 6.32(t, J=2.5 Hz, 1H, C(3)H).

$^{11}$B NMR (CDCl$_3$, 115.5 MHz): δ 32.3

$^{13}$C NMR (CDCl$_3$, 100.6 MHz): δ 12.7, 13.0(broad), 45.9, 93.0(broad), 117.3, 121.6, 122.7, 124.0, 126.9.

Example 6

Preparation of (3a,7a-azaborindenyl)(pentamethylcyclopentadienyl)zirconium dichloride

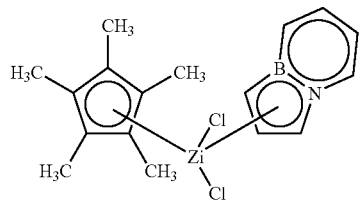

A) 3a,7a-Azaborindene

A solution of 4,7-Dihydro-4a,7a-azaborindene (Ex. 5C), 4.5 g, 37.8 mol) in 25 mL pentane was added to a suspension of 2,3-dichloro-5,6-dicyano-1,4-benzoquinone (10.4 g, 45.6 mol) in 50 mL of pentane. The mixture was stirred at 25° C. for 10 hours after which the solid was removed by filtration. The filtrate was distilled affording the desired product (1.3 g, 30 percent) bp=26° C. at 0.1 torr.

HRMS: Calculated for C$_7$H$_{10}$$^{11}$BN: 117.0750. Found 117.0752.

$^1$H NMR (C$_6$D$_6$, 400 MHz): δ 3.52 (broad, s, 2H, CH$_2$N), 6.11 (t, J=6.3 Hz, 1H, C(5)H), 6.52 (m, 2H, C(1)HC(2)H), 6.94(d, J=6.3, 1H, C(4)H), 7.06(d, J=11.1 Hz, 1H, BCH), 7.61(dd, J=11.1, 6.3 Hz, 1H, C(6)H).

$^{11}$B NMR (C$_6$D$_6$, 115.5 MHz): δ 34.2

$^{13}$C NMR (C$_6$D$_6$, 100.5 MHz): δ 58.8, 109.5, 124(broad), 133.6(broad), 135.3, 143.2, 144.2.

B) (3a,7a-azaborindenyl)(pentamethylcyclopentadienyl)zirconium dichloride

In substantially the same manner as for Example 5, step D), 3a,7a-azaborindene (0.30 g, 2.56 mmol) and pentamethylcyclopentadienylzirconium trichloride (0.85 g, 2.56 mmol) were contacted to give the desired product (0.63 g, 60 percent). The structure was confirmed by X-ray crystallography.

$^1$H NMR (CD$_2$cl$_2$, 400 MHz): δ 2.00(s, 15H, CpMe), 4.85(dd, J=5.1, 1.8 Hz, 1H, C(1)H), 6.27 (dd, J=5.3, 2.4 Hz, 1H, C(2)H), 6.58 (td, J=6.6, 1.1 Hz, 1H, C(5)H), 6.82(t, J=2.4 Hz, 1H, C(3)H), 7.15(d, J=11.7 Hz, 1H, C(7)H), 7.36(dd, J=11.7, 6.4 Hz, 1H, C(6)H), 7.64 (dd, J=6.0, 1.0 Hz, 1H, C(4)H).

$^{11}$B NMR (CD$_2$Cl$_2$, 115.5 Mz): δ 23.8

$^{13}$C NMR (CD$_2$Cl$_2$, 100.5 MHz): δ 12.6, 115.4, 115.8, 121.5, 129.6, 136.9.

Ethylene/1-Octene Polymerization Conditions

All liquid and gas feeds were passed through columns of alumina and a decontaminant (Q-5™ catalyst available from Englehardt Chemicals Inc.) prior to introduction into the reactor. Catalyst components are handled in a glovebox containing an atmosphere of argon or nitrogen. A stirred 2.0 liter reactor is charged with 740 g of mixed alkanes solvent and 118 g of 1-octene comonomer. Hydrogen (25 psi, 170 kPa) is added as a molecular weight control agent by differential pressure expansion from a 75 mL addition tank. The reactor is heated to 140° C. and saturated with ethylene at 500 psig (3.4 MPa). Metal complex as dilute toluene solution and cocatalyst as dilute solutions in hexane, were mixed and transferred to a catalyst addition tank and injected into the reactor. The cocatalyst was methylalumoxane used in a 1000:1 molar ratio to the catalyst. The polymerization conditions were maintained for 15 minutes with ethylene added on demand. The resulting solution was removed from the reactor, quenched with isopropyl alcohol, and stabilized by addition of a toluene solution containing 67 mg/100 g polymer of a hindered phenol antioxisant (Irganox™ 1010 from Ciba Geigy Corporation) and 133 mg/100 g polymer of a phosphorus stabilizer (Irgafos 168 from Ciba Geigy Corporation).

Between sequential polymerization runs, a wash cycle was conducted in which 850 g of mixed alkanes was added to the reactor and the reactor was heated to 150° C. The reactor was then emptied of the heated solvent immediately before beginning a new polymerization run.

Polymers were recovered by drying in a vacuum oven set at 140° C. for 20 hours. Density values are derived by determining the polymer's mass when in air and when immersed in methylethyl ketone. Micro melt index values (MS) are obtained using a Custom Scientific Instrument Inc. Model CS-127MF-015 apparatus at 190° C., and are unit less values calculated as follows: MMI=1/(0.00343 t−0.00251), where t=time in seconds as measured by the instrument. Results are contained in Table 1.

TABLE 1

| Run | Catalyst (μmol) | Time (minutes) | Yield (g) | Efficiency[1] | Tm (° C.) | MMI[2] |
|---|---|---|---|---|---|---|
| 1 | Ex. 1 (0.75) | 15 | 58.4 | 78 | — | 70 |
| 2 | Ex. 2 (1.0) | 17 | 90.79 | 91 | 131.5 | 60 |
| 3 | Ex. 3 (1.0) | 15 | 22.0 | 22 | 126.5 | >100 |
| 4 | Ex. 4 (1.0) | 16 | 41.8 | 42 | 129.3 | >100 |
| 5 | Ex. 5 (2.0) | 16 | 45.1 | 22 | 133.2 | >100 |
| 6 | Ex. 6 (1.0) | 15 | 40.0 | 40 | 132 | 72 |

[1]efficiency, g polymer/ μmole zirconium
[2]micro melt index 190° C., (comparative technique of melt index determination)

Propylene Conditions

Batch reactor polymerizations were conducted in a two liter Parr reactor equipped with an electrical heating jacket, internal serpentine coil for cooling, and a bottom drain valve. Pressures, temperatures and block valves were computer monitored and controlled. Mixed alkanes (650 g) was measured in a solvent shot tank fitted with a differential pressure transducer or weigh cell. It was then added to the reactor from the solvent shot tank. Propylene, 150 g, was measured using a mass flow meter. The contents of the reactor was stirred at 1200 rpm. Hydrogen was added by differential expansion (Δ 25 psi, 170 kPa) from a 75 ml shot tank initially at 300 psig (2.2 MPa). The contents of the reactor were then heated to the desired run temperature. The catalyst (as 0.0050 M solution in toluene) and MAO cocatalyst were combined in a one to one thousand molar ratio in the glove box and transferred from the glove box to the catalyst shot tank through 1/16 in (0.16 cm) tubing using toluene to aid in the transfer. The catalyst tank was then pressurized to 350 psig (2.5 MNa) using nitrogen. After the contents of the reactor had stabilized at the desired run temperature of 70° C., 18 μmol of the catalyst was injected into the reactor via a dip tube. The temperature was maintained by allowing cold glycol to pass through the internal cooling coils. The reaction was allowed to proceed for 46 minutes. The contents of the reactor were then expelled into a 4 liter nitrogen purged vessel and quenched with isopropyl alcohol and 100 mg of Irganox 1010 in toluene was added as an antioxidant. Volatile materials were removed from the polymer in a vacuum oven up to 140° C. overnight and cooled to at least 50° C. prior to removal from the oven. The yield of isotactic polypropylene was 41.9 g, giving an efficiency of 2.3 g/μmol Zr.

The invention claimed is:

1. A metal complex corresponding to the formula, $CpM(X)_x(L)_t(X')_{x'}$, (I), where Cp is a 1,2-azaborolyl anionic ligand, corresponding to the formula:

wherein, $R^A$, independently each occurrence, is a group of from 1 to 40 atoms, not counting hydrogen, selected from the group consisting of hydrocarbyl, trihydrocarbylsilylhydrocarbyl, dihydrocarbylamino, and hydrocarbyleneamino, and optionally two $R^A$ groups may be joined together thereby forming a fused multi-ring ligand group;

$R^B$, independently each occurrence, is selected from the group consisting of hydrogen, Z'Y and $R^A$, with the proviso that one $R^B$ is Z'Y, said Cp also being bound to M;

M is a metal selected from Groups 3–10 or the Lanthanide series of the Periodic Table of the Elements;

Z'Y is a divalent moiety with Z' bonded to Cp and Y covalently or coordinate covalently bonded to M, wherein, Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

Y is —O—, —S—, —$NR^5$—, —$PR^5$—; —$NR^5_2$, or —$PR^5_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

L" is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

x is 0, 1, 2, or 3;

t is a number from 0 to 2, and x' is 0 or 1.

2. A metal complex according to claim 1 wherein two $R^A$ groups are joined together thereby forming a fused multi-ring ligand group.

3. A metal complex according to claim 1, corresponding to the formula:

where M is a Group 4 metal that is in the +2, +3 or +4 formal oxidation state;

$R^A$ independently each occurrence is a hydrocarbyl, dihydrocarbylamino, or hydrocarbyleneamino group of from 1 to 40 atoms, not counting hydrogen, or two or more $R^A$ groups may be covalently linked together;

$R^B$ independently each occurrence is hydrogen or $R^A$;

Z' is $SiR^6_2$, $CR^6_2$, $SiR^6_2SiR^6_2$, $CR^6_2CR^6_2$, $CR^6=CR^6$, or $BR^6$;

Y is —$NR^5$—, —$PR^5$—; —$NR^5_2$, or —$PR^5_2$;

$R^5$, independently each occurrence, is $C_{1-20}$ hydrocarbyl;

$R^6$, independently each occurrence, is hydrogen, or $C_{1-20}$ hydrocarbyl;

X is an anionic or dianionic ligand group having up to 60 atoms exclusive of the class of ligands that are cyclic, delocalized, π-bound ligand groups;

X' independently each occurrence is a neutral ligand having up to 40 atoms;

p is zero, 1 or 2, and is two less than the formal oxidation state of M when X is an anionic ligand, and when X is a dianionic ligand group, p is 1; and q is zero, 1 or 2.

4. A metal complex according to claim 3 wherein:

X is halo, $C_{1-10}$ hydrocarbyl or trialkylsilylalkyl of up to 20 carbons, or two such X groups together form a divalent ligand group;

$R^A$ independently each occurrence is hydrocarbyl or two adjacent $R^A$ groups are joined together forming a fused ring;

$R^B$ is $C_{1-10}$ hydrocarbyl;

Y is $-NR^E-$ where $R^E$ is $C_{1-6}$ alkyl or cycloalkyl; and

Z' is $SiR^6{}_2$ where $R^6$ is methyl, phenyl, or $C_{1-10}$ alkylphenyl.

5. A metal complex according to claim 1 wherein X is chloro, methyl, benzyl, trimethylsilylmethyl, or two X groups together are (dimethylsilylene)bis(methylene).

6. A metal complex according to claim 3 wherein M is titanium.

7. A catalyst composition comprising (A) the metal complex of any one of claims 1-5 or 6 and (B) an activating cocatalyst, or a reaction product thereof, wherein the molar ratio of (A) to (B) is from 1:10,000 to 100:1.

8. A process for polymerizing one or more addition polymerizable monomers, comprising contacting said monomer or a mixture of such monomers under polymerization conditions with a catalyst composition according to claim 7.

* * * * *